US00PP15931P3

(12) United States Plant Patent
Miyazaki et al.

(10) Patent No.: US PP15,931 P3
(45) Date of Patent: Aug. 30, 2005

(54) *PETUNIA* PLANT NAMED 'SUNBAPIVE'

(50) Latin Name: *Petunia hybrida*
Varietal Denomination: Sunbapive

(75) Inventors: Kiyoshi Miyazaki, Hikone (JP); Kazunari Iwaki, Omihachiman (JP); Takuro Ishihara, Yokaichi (JP)

(73) Assignee: Suntory Flowers Limited, Tokyo (JP)

( * ) Notice: Subject to any disclaimer, the term of this patent is extended or adjusted under 35 U.S.C. 154(b) by 102 days.

(21) Appl. No.: 10/699,570

(22) Filed: Oct. 30, 2003

(65) Prior Publication Data

US 2005/0097646 P1 May 5, 2005

(51) Int. Cl.[7] ..... A01H 5/00
(52) U.S. Cl. ..... Plt./356
(58) Field of Search ..... Plt./356

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP9,322 | P | 10/1995 | Tachibaba et al. |
| PP9,341 | P | 10/1995 | Tachibaba et al. |
| 5,523,520 | A | 6/1996 | Hunsperger et al. |
| PP10,904 | P | 5/1999 | Hansson |

FOREIGN PATENT DOCUMENTS

| | | |
|---|---|---|
| JP | PBR Reg. No. 4009 | 3/1994 |
| JP | PBR Reg. No. 7390 | 9/1999 |

OTHER PUBLICATIONS

Goldsmith Seeds 2003–2004 Catalog, p. 46, Published by Goldsmith Seeds Inc., USA.

*Primary Examiner*—Anne Marie Grunberg
*Assistant Examiner*—Annette H Para
(74) *Attorney, Agent, or Firm*—Christie, Parker and Hale, LLP

(57) ABSTRACT

Disclosed herein is a new and distinct variety of a *Petunia* plant having a decumbent growth habit and long stems. The *Petunia* plant has abundant branching, and a great profusion of blooms, the whole plant remaining in bloom for a considerable period of time. The flowers are single and small, the petals having a deep purplish pink color with strong reddish purple vein. The bottom color of the corolla throat is dark purple and the outside of the corolla tube is moderate purple. The plant exhibits high resistance to rain, heat, cold and disease.

2 Drawing Sheets

Botanical/commercial classification: *Petunia hybrida*/*Petunia* plant.
Varietal denomination: cv. 'Sunbapive'.

BACKGROUND OF THE VARIETY

The present invention relates to a new and distinct variety of *petunia* plant originated from the crossing a seedling called 'Fantasy Crystal Red' (♀) and a wild type *Petunia* plant called '1792' (♂).

The *Petunia* is a very popular plant that is used for flower bedding and potting in the summer season. There are only a few *Petunia* varieties which do not have an upright growth habit and which have a high resistance to rain, heat, and diseases. The *Petunia* plants of the 'Revolution' series include 'Revolution Purple pink' (U.S. Plant Pat. No. 6,915), 'Revolution Brilliant pink' (U.S. Plant Pat. No. 6,914), 'Revolution Brilliant pink-mini' (U.S. Plant Pat. No. 6,899), and 'Revolution Blue vein' (U.S. Plant Pat. No. 9,322). These are decumbent type plants having long stems, a lower plant height, abundant branching, and a high resistance to heat, rain and disease. However, there are only a few *Petunia* varieties having a great profusion of flowers, vivid colored and vein patterned flower petals and a high resistance to rain, heat, and diseases. Accordingly, this invention was aimed at obtaining a new variety having vivid purple pink colored petals with vivid reddish purple vein together with the above features.

The new variety of *petunia* plant according to this invention originated from crossing a seedling called 'Fantasy Crystal Red' (♀) and a wild type *Petunia* plant called '1792' (♂). The seed of 'Fantasy Crystal Red' was bought from Sakata Seed Ltd. '1792' (non-patented in the United States) is a decumbent, wild type *Petunia* plant native to Brazil.

In April 1998, crossing 'Fantasy Crystal Red' as female parent and '1792' as pollen parent was conducted at the Yokaichi-shi, Shiga,. In January 1999, 120 seedlings were obtained from that crossing. These seedlings were grown in pots under glass and tested. One individual plant was selected in view of its decumbent growth habit and its flower color. That seedling was propagated by cutting from July 1999, and a trial by flower potting and bedding was carried out from April 2000, at the Yokaichi-shi, Shiga. The botanical characteristics of that plant were then examined, using similar varieties 'Revolution Pinkvein' (U.S. Plant Pat. No. 9,341) and 'Revolution Marrose' (U.S. Plant Pat. No. 10,904) for comparison. As a result, it was concluded that this *petunia* plant is distinguishable from any other variety whose existence is known to us, and is uniform and stable in its characteristics. The new variety of *petunia* plant was named 'Sunbapive'.

In the following description, the color-coding is in accordance with The Horticultural Colour Chart of The Royal Horticultural Society, London, England (R.H.S. Color Chart).

The female parent used in the crossing of 'Sunbapive' called 'Fantasy Crystal Red' has an erect growth habit while that of the new variety is decumbent. The branching is fewer than the new variety. It has small single flowers, the petals having a vivid red (R.H.S. 52A) color with strong red (R.H.S. 53C) vein. The bottom color of the corolla throat is dark red (R.H.S. 183A) and outside color of the corolla tube is moderate red (R.H.S. 181B).

The main botanical characteristics of 'Fantasy Crystal Red' are as follows:

Plant:
- *Growth habit.*—Erect.
- *Plant height.*—Approximately 15.5 cm.
- *Spreading area of plant.*—Small.
- *Blooming period.*—April to July in the southern Kanto area, Japan.

Stem:
- *Length.*—Approximately 9.5 cm.
- *Thickness.*—Main stem approximately 2.8 mm.
- *Pubescence.*—Sparse.
- *Branching.*—Medium.
- *Internode length.*—Approximately 2.2 cm.
- *Color.*—Light yellow green (R.H.S. 145C).

Leaf:
- *Whole shape.*—Elliptic. The apex shape is acute, and the base shape is attenuate.
- *Length.*—Approximately 3.2 cm.
- *Width.*—Approximately 2.2 cm.
- *Color.*—Upper-side color is strong yellow green (R.H.S. 144A). Bottom-side color is moderate yellow green (R.H.S. 147B).
- *Pubescence.*—Sparse.

Flower:
- *Facing direction.*—Slightly slanted upward.
- *Type.*—Single.
- *Shape.*—Funnel-shape, with five-fissured limb.
- *Shape of petal tip.*—Obtuse.
- *Petal margin.*—Weakly by undulating.
- *Diameter.*—Approximately 4.5 cm.
- *Color.*—Petal; vivid red (R.H.S. 52A) with strong red (R.H.S. 53C) vein. Bottom color of the corolla throat; dark red (R.H.S. 183A). Outside color of the corolla tube; moderate red (R.H.S. 181B).
- *Reproductive organs.*—1 normal pistil and 5 normal stamens. Color of pistil is vivid yellow green (R.H.S. 144B). Color of stamen is pale yellow (R.H.S. 158C).
- *Peduncle.*—Approximately 1.0 mm in thickness, and approximately 1.0 cm in length.
- *Physiological and ecological characteristics.*—Moderate resistance to cold, rain, pests and disease.

The male parent '1792' used in the crossing of 'Sunbapive' was a wild type *petunia* plant originated from Brazil. The *petunia* plant '1792' having a decumbent growth habit with long stems and many branches. The leaf is very small without petiole. It has very small single flower, the petals having a yellowish White (R.H.S. 158D) color with strong reddish purple (R.H.S. 72B) vein.

The main botanical characteristics of the '1792' are as follows:

Plant:
- *Growth habit.*—Decumbent.
- *Plant height.*—Approximately 5.5 cm.
- *Spreading area of plant.*—Large.
- *Blooming period.*—May to August in the southern Kanto area, Japan.

Stem:
- *Length.*—15.0 cm.
- *Thickness.*—Approximately 1.3 mm.
- *Pubescence.*—Normal.
- *Branching.*—Many.
- *Internode length.*—Approximately 1.0 cm.
- *Color.*—Strong yellow green (R.H.S. 144B).

Leaf:
- *Whole shape.*—Elliptic. The apex shape is acute, and the base shape is attenuate.
- *Length.*—Approximately 2.5 cm.
- *Width.*—Approximately 1.5 cm.
- *Color.*—Upper-side color is strong yellow green (R.H.S. 143A). Bottom-side color is moderate yellow green (R.H.S. 147B).
- *Pubescence.*—Sparse.

Flower:
- *Facing direction.*—Horizontal.
- *Type.*—Single.
- *Shape.*—Funnel-shape, with five-fissured limb.
- *Shape of petal tip.*—Rounded.
- *Petal margin.*—Weakly by undulating.
- *Diameter.*—Approximately 4.3 cm.
- *Color.*—Petal; Yellowish White (R.H.S. 158D) with strong reddish purple (R.H.S. 72B) vein. Bottom color of the corolla throat; greenish white (R.H.S. 155C). Outside color of the corolla tube; brilliant yellow green (R.H.S. 145B).
- *Reproductive organs.*—1 normal pistil and 5 normal stamens. Color of pistil is strong yellow green (R.H.S. 144B). Color of stamen is light olive gray (R.H.S. 197C).
- *Peduncle.*—Approximately 1.0 mm in thickness, and approximately 2.4 cm in length.
- *Physiological and ecological characteristics.*—Moderate resistance to cold and pest. Strong resistance to rain, heat and diseases.

The main botanical characteristics of similar variety 'Revolution Pinkvein' used for examination as comparison are as follows:

Plant:
- *Growth habit.*—Decumbent.
- *Plant height.*—Approximately 14.5 cm.
- *Spreading area of plant.*—Large.
- *Blooming period.*—May to August in the southern Kanto area, Japan.

Stem:
- *Length.*—Approximately 15 cm.
- *Thickness.*—Main stem approximately 1.6 mm.
- *Pubescence.*—Normal.
- *Branching.*—Many.
- *Internode length.*—Approximately 0.6 cm.
- *Color.*—Strong yellow green (R.H.S. 144B).

Leaf:
- *Whole shape.*—Elliptic. The apex shape is acute, and the base shape is attenuate.
- *Length.*—Approximately 7.9 cm.
- *Width.*—Approximately 3.5 cm.
- *Color.*—Upper-side color is dark yellow green (R.H.S. 146A). Bottom-side color is moderate yellow green (R.H.S. 147B).
- *Pubescence.*—Normal.

Flower:

*Facing direction.*—Slantly upward.

*Type.*—Single.

*Shape.*—Funnel-shape, with five-fissured limb.

*Shape of petal tip.*—Rounded.

*Waving of petal.*—Weak.

*Diameter.*—Approximately 5.2 cm.

*Color.*—Petal; Deep purplish pink (R.H.S. 70C) with strong reddish purple (R.H.S. 72A) vein. Bottom color of the corolla throat is dark reddish purple (R.H.S. 79A). Outside color of the corolla tube is light reddish purple (R.H.S. 78C).

*Reproductive organs.*—1 normal pistil and 5 normal stamens. Color of pistil is grayish olive green (R.H.S. 137A). Color of stamen is deep purple (R.H.S. 86A).

*Peduncle.*—Approximately 1.6 mm in thickness, and approximately 1.8 cm in length.

*Physiological and ecological characteristics.*—Strong resistance to cold, heat, rain and diseases. Moderate resistance to pests.

The main botanical characteristics of similar variety 'Revolution Marrose' used for examination as comparison are as follows:

Plant:

*Growth habit.*—Decumbent.

*Plant height.*—Approximately 20 cm.

*Spreading area of plant.*—Large.

*Blooming period.*—April to September in the southern Kanto area, Japan.

Stem:

*Length.*—Approximately 20 cm.

*Thickness.*—Main stem approximately 3.0 mm.

*Pubescence.*—Normal.

*Branching.*—Many.

*Internode length.*—Approximately 3.0 cm.

*Color.*—Light yellow green (R.H.S. 145C).

Leaf:

*Whole shape.*—Lanceolate. The apex shape is acute, and the base shape is attenuate.

*Length.*—Approximately 5.5 cm.

*Width.*—Approximately 3.5 cm.

*Color.*—Upper-side color is dark yellow green (R.H.S.146A). Bottom-side color is moderate yellow green (R.H.S. 147B).

*Pubescence.*—Normal.

Flower:

*Facing direction.*—Slantly upward.

*Type.*—Single.

*Shape.*—Funnel-shape, with five-fissured limb.

*Shape of petal tip.*—Acute.

*Lobation.*—Medium.

*Waving of petal.*—Weak.

*Diameter.*—Approximately 7.5 cm.

*Color.*—Petal; strong purplish pink (R.H.S. 61D) with red purple (R.H.S. 79B) vein. Bottom color of the corolla throat; deep purple (R.H.S. 86A). Outside color of the corolla tube; strong purplish pink (R.H.S. 61D).

*Reproductive organs.*—1 normal pistil and 5 normal stamens. Color of pistil is grayish olive green (R.H.S. 137A). Color of stamen is deep purple (R.H.S. 86A).

*Peduncle.*—Approximately 1.5 mm in thickness, and approximately 2.0 cm in length.

*Physiological and ecological characteristics.*—Strong resistance to cold, heat, rain and diseases. Moderate resistance to pests.

SUMMARY OF THE VARIETY

The new variety of the *petunia* plant has a decumbent growth habit, abundant branches and a great profusion of blooms with the whole plant remaining in bloom for a considerable period of time. The flowers are single and small. The petal color is deep purplish pink with strong reddish purple vein. The plant has a high resistance to rain, cold, heat and diseases.

BRIEF DESCRIPTION OF THE PHOTOGRAPH

DESCRIPTION OF THE NEW VARIETY

Figure 1:
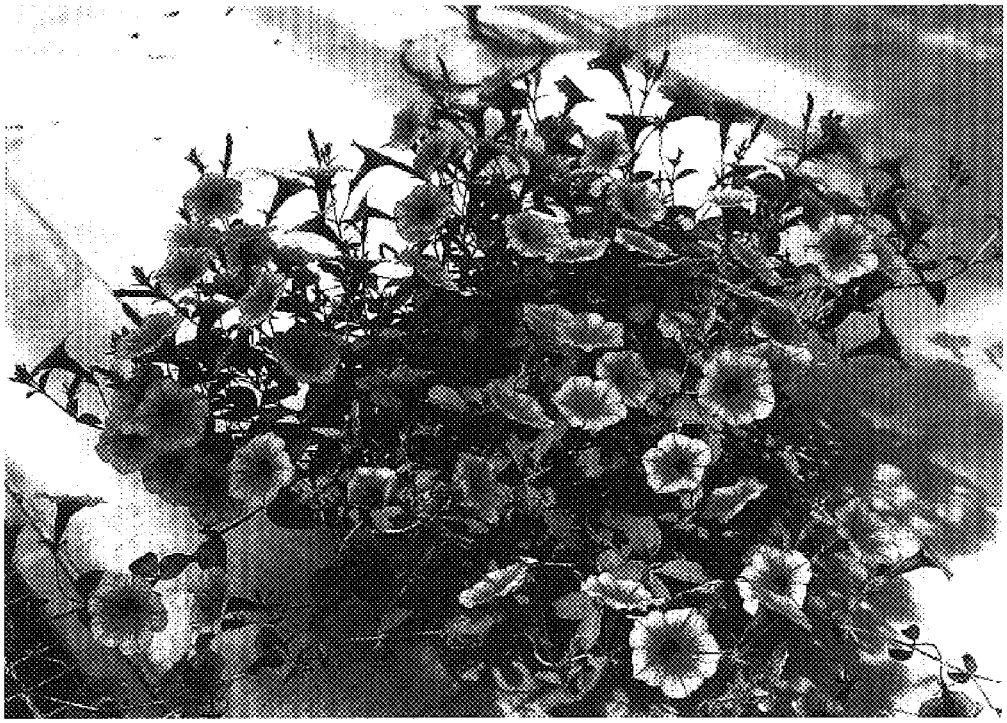
FIG. 1 is a photograph of flowers and leaves of the new variety of *Petunia* plant 'Sunbapive'.
Figure 2:
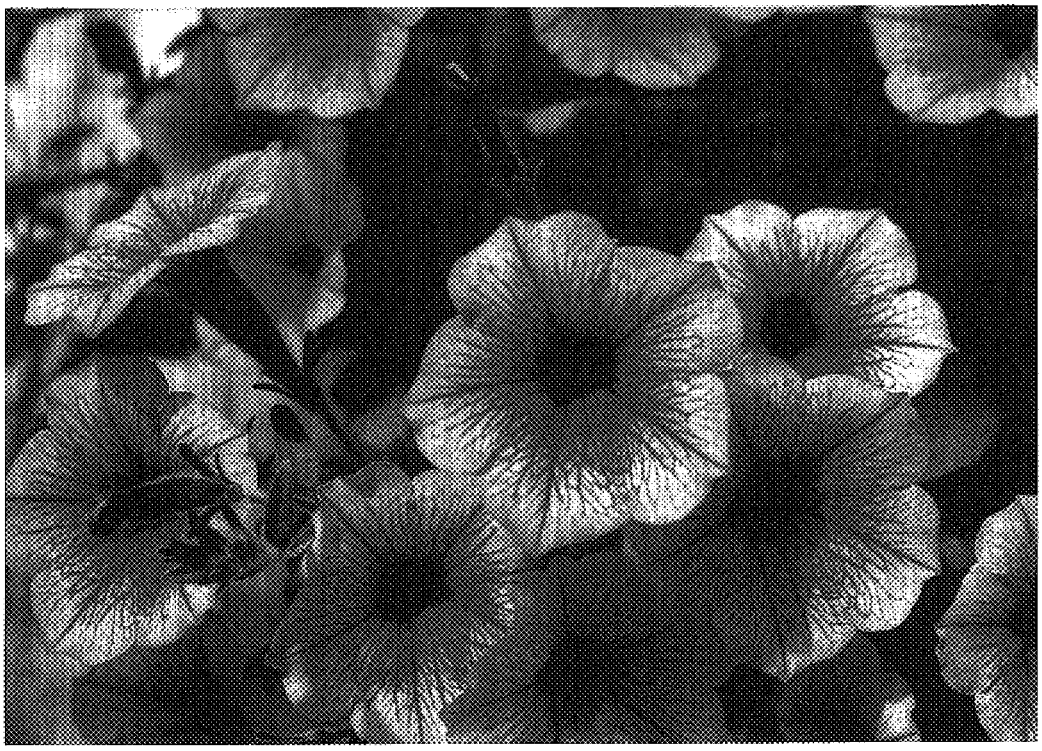
FIG. 2 is a close-up photograph of flowers of the new variety of *Petunia* plant 'Sunbapive'.

The botanical characteristics of the new and distinct variety of *Petunia* plant named 'Sunbapive', grown in Yokaichi-shi, Shiga, Japan are as follows.

Plant:

*Growth habit.*—Decumbent.

*Plant height.*—Approximately 21 cm.

*Spreading area of plant.*—Large.

*Blooming period.*—Early April to late October in the southern Kanto area, Japan. The plant shape does not change throughout this period. A typical flower commonly lasts approximately 5 days on the plant when experiencing a temperature of approximately 20° C.

Stem:

*Length.*—Approximately 15 cm.

*Thickness.*—Approximately 2.2 mm.

*Pubescence.*—Normal.

*Branching.*—Many.

*Internode length.*—Approximately 2.5 cm.

*Color.*—Light yellow green (R.H.S. 145C).

Leaf:

*Whole shape.*—Lanceolate. The apex shape is acute, and the base shape is attenuate.

*Length.*—Approximately 4.6 cm.

*Width.*—2.1 cm.

*Color.*—Upper side color is dark yellow green (R.H.S. 146A). Bottom side color is moderate yellow green (R.H.S. 147B).

*Thickness.*—Approximately 0.7 mm.

*Pubescence.*—Normal. Flower Opens slightly obliquely upward (flower faces slanted upwards).

*Type.*—Single.

*Shape.*—Funnel-shape, with five-fissured limb.

*Shape of petal tip.*—Rounded.

*Petal.*—Length from the throat approximately 2.0 cm.; petal width approximately 2.5 cm; apex shape is cupsidate; margin is entire.

*Petal margin.*—Weakly undulating.

*Diameter.*—Approximately 4.5 cm.

*Color.*—Petal; deep purplish pink (R.H.S. 68A) with strong reddish purple (R.H.S. 72B) vein. Bottom color of the corolla throat; dark purple (R.H.S. 79A).

Outside color of the corolla tube; moderate purple (R.H.S. 83B).

*Petiole.*—Length approximately 6.0 mm.; width approximately 1.5 mm.; diameter approximately 1.0 mm.

*Sepal.*—Length approximately 1.3 cm.; width approximately 2.0 mm, shape narrowly oblong; apex shape obtuse; margin is entire.

*Reproductive organs.*—1 normal pistil and 5 normal stamens. Color of pistil is grayish yellow green (R.H.S. 137A). Color of stamen is deep purple (R.H.S. 86A).

*Peduncle.*—Approximately 1 mm in diameter and approximately 4.0 cm in length; texture is pubescent and smooth.

*Physiological and ecological characteristics.*—High resistance to rain, cold, heat and diseases. Moderate resistance to pests. USDA Hardiness Zone of the instant variety is 9. The plant grows well at temperatures up to 30° C. The applicant has not evaluated the lower and upper temperature for the plant survival. No serious damage by white fly, aphids, fungus and bacterial disease has been observed.

This new variety of *Petunia* plant is most suitable for flower bedding and potting, particularly in hanging pots or planters, and is excellent for use as ground cover. Pinching of old blossoms will enhance the formation of new blossoms.

We claim:

1. A new and distinct variety of *Petunia* plant named 'Sunbapive', substantially as herein illustrated and described.

* * * * *